May 2, 1939. H. TROPSCH Re. 21,073
CONVERSION OF HYDROCARBONS
Original Filed Dec. 15, 1933
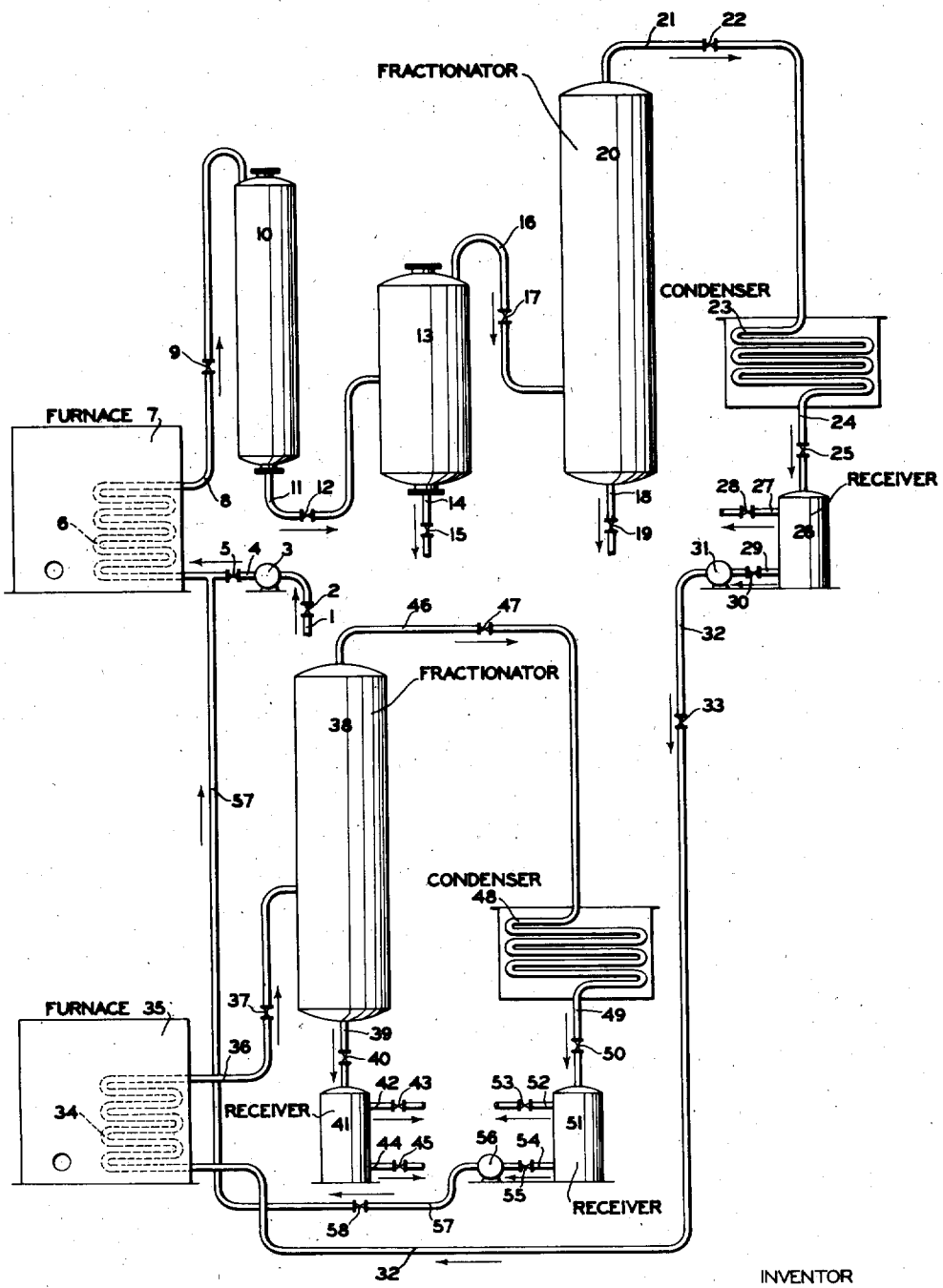
INVENTOR
HANS TROPSCH
BY
ATTORNEY Reissued May 2, 1939

Re. 21,073

UNITED STATES PATENT OFFICE 21,073

CONVERSION OF HYDROCARBONS

Hans Tropsch, deceased, late of Chicago, Ill., by Carl W. von Helmolt, Chicago, Ill., administrator de bonis non, assignor to Universal Oil Products Company, Chicago, Ill., a corporation of Delaware Original No. 2,069,785, dated February 9, 1937, Serial No. 702,433, December 15, 1933. Application for reissue August 1, 1938, Serial No. 222,476

14 Claims. (Cl. 196—10)

This invention relates more particularly to the conversion of the propane-butane fractions of hydrocarbon gas mixtures such as, for example, natural gas, gas mixtures produced incidental to the primary distillation of crude petroleums and the fixed gases produced in cracking operations upon heavy hydrocarbon oils. The term "propane-butane fraction" is thus intended to include fractions containing the corresponding olefins, (propylene and the butylenes) which will constitute a varying proportion of cracked gases. It is also intended to include fractions produced from stabilizer units operating upon either straight run or cracked gasolines which have the approximate composition of propane-butane mixtures although the boiling range may be somewhat wider in these cases due to crude fractionation, e. g. may contain small percentages of lower boiling members of the group such as ethane and methane and some higher boiling members, such as pentane. Pentanes and amylenes representing five carbon atom hydrocarbons are not objectionable in charging stocks to be treated by the present invention, but it is preferred that methane and ethane be absent or only minor amounts be present as they are distinctly detrimental as will be developed later in the description.

In a more specific sense the invention is concerned with a pyrolytic process for efficiently converting propane-butane fractions into commercial yields of good anti-knock gasoline, the limiting conditions of operation under which optimum conversion into desired gasoline liquids is obtained being a particular feature of the process.

The hydrocarbon fractions which serve as the charging material according to the present invention are too light for blending in gasoline above a certain limit. Also, the total quantities of such gases produced in petroleum refining operations, including cracking, is very large and, from the standpoint of the refiner, they are usually looked upon as a waste product since, from a fuel standpoint, they are produced in excess of requirements for the heating of cracking processes and frequently for the total heating of all refinery distilling units, and in many cases low grade fuels are available.

A more profitable utilization of these propane-butane fractions is, therefore, a matter of some importance and the present invention is a contribution to this field.

In one specific embodiment the present invention comprises heating hydrocarbon mixtures consisting essentially of compounds of 3 and 4 carbon atoms under selected elevated temperature and pressure conditions, passing the heated products through an enlarged reaction zone in which they are maintained at substantially constant pressure and temperature conditions for a time necessary for the completion of desired conversion and polymerizing reactions, subjecting the products of conversion to fractionation at lowered pressure to segregate fixed gases comprising essentially hydrogen, methane, ethane and ethylene which are removed from the process, an intermediate fraction consisting essentially of 3 and 4 carbon atom hydrocarbons which is returned to the heated zone for further conversion and liquids of gasoline boiling range constituting the desired product of the process.

The range and inter-relation of time, temperature, pressure, etc., under which the production of gasoline from 3 and 4 carbon atom hydrocarbons is accomplished will be brought out in the following description of the sequence of operating steps given in connection with a particular plant hookup shown in the attached diagrammatic drawing in which interconnected elements are represented by conventional figures in side elevation not drawn to scale.

Referring to the drawing hydrocarbon charging stocks of the general character previously designated (which will be hereinafter referred to as "propane-butane" mixtures) may be introduced to the plant by way of line 1, containing control valve 2, and pumped by a pump 3 through a line 4 containing a control valve 5 into and through a properly designed tubular heating element 6 positioned in a furnace 7. During passage of the gases through the heating element and the subsequent reaction zone, the inter-related factors of temperature, pressure and time are so controlled that about 50 to 80% by weight of the original charge appears later as intermediate recycle stock. It has been found that if higher rates of conversion per pass occur not only is the ultimate yield of liquefiable gasoline hydrocarbons reduced, but also carbon troubles are encountered in the heating element so that dangerous overheating of the tubes may take place unless frequent shutdown periods are observed. Furthermore, by proper control of the operating conditions while maintaining a restricted conversion per pass, the formation of heavy tars may be practically eliminated so that these ordinarily useless byproducts of cracking are not formed. If lower rates of conversion per pass are employed it has been found that the equipment may be too large for economy. As a general average, when dealing with propane-butane mixtures ordinarily obtained from stabilizer units, the production of 60% recycle stock is an average figure for best overall yields.

The temperature range employed at the exit of the heating element is from 450 to 575° C., in a majority of cases from 525 to 550° C., and the pressure may vary from approximately 25 to 100 atmospheres, though as a rule when dealing with the commoner propane-butane blends 50 to 75 atmospheres produce optimum results in respect to yield of gasoline. In regard to temperature, it may be noted that the lower ranges are preferable when the gas treated, for example, a gas from an oil cracking plant, contains a relatively high percentage of olefins, say from 30 to 40%, while the higher temperatures accomplish more desirable effects when the olefin content of the original gases is low or approximately from 0 to 20% volume concentration. The time under which the reacting substances are maintained under these temperature and pressure conditions may vary from approximately 40 to 120 seconds, this factor having been found to be related to the olefin content of the gaseous recycle products of the conversion step, which point will be discussed more at length in connection with the recycle stock.

The heated products from the heating element 6 pass through transfer line 8, containing control valve 9, and enter a reaction zone 10 without substantial pressure reduction other than a slight differential drop due to fluid friction in the line. The reactions of polymerization which occur in this chamber are of an exothermic character and for best results the chamber may be cooled somewhat to maintain the optimum polymerizing temperature for the production of gasoline boiling range liquids rather than heavier polymers which are of too high boiling range for use in gasoline. The cooling may be brought about by controlled exposure of the chamber to atmospheric conditions or by placing indirect heat exchange coils in the chamber through which if desired the incoming charge may be pumped countercurrently.

The products from the reaction zone comprising fixed gases, gasoline and small amounts of heavier polymers is then conducted through line 11, containing control valve 12, to a chamber 13 provided principally as a separator for any heavy tars which are settled and withdrawn through line 14, containing control valve 15. The pressure is preferably reduced at valve 12 to some point within the range of 150 to 300 pounds per square inch, depending upon the relative amounts of the three types of products, to-wit, gases of two carbon atoms and less, intermediate recycle stock consisting of compounds of 3 and 4 carbon atoms and gasoline hydrocarbons. Within this pressure range at ordinary temperatures, it is found that the intermediate recycle stock compounds are liquid either alone or at least completely soluble in the condensed gasoline.

The vaporous products from the tar separator pass through line 16, containing control valve 17, to a fractionator 20 which is operated to finally separate compounds heavier than gasoline and of the character of intermediate petroleum distillates which are withdrawn through line 18, containing control valve 19, to any use for which they are suited, while the overhead vapors comprising the major portion of the admitted products pass through line 21, control valve 22 condenser 23, line 24 and valve 25 to receiver 26 which is preferably maintained under the same pressure as that in the preceding tar separator and fractionator, allowing for differential drops.

Under a pressure range of approximately 150 to 300 pounds the gaseous products present in receiver 26 are found to consist principally of hydrogen, methane, ethane and ethylene, and as a rule the separation is sufficiently sharp so that these gases may be withdrawn more or less completely from the receiver through line 27, containing control valve 28. The removal of the hydrogen and the low molecular weight paraffins at this point is of positive value while the loss of ethylene is of no consequence since this compound does not polymerize to any great extent to form gasoline under the preferred conditions of operation.

The liquids in receiver 26 comprising essentially propane, propylene, butanes, butylenes, and liquid gasoline hydrocarbons is then taken by pump 31 through line 29, containing control valve 30 and subjected to treatment aimed at the segregation of 3 and 4 carbon atom recycle stock and the desired gasoline product.

The discharge from pump 31 passing through line 32 and control valve 33 therein is separated into recycle stock and finished gasoline by any one of the general methods of stabilization in current use. The question of the temperature and pressure employed in the fractionation to remove substantially all 3 and 4 carbon atom hydrocarbons will depend upon their percentage in the mixture, the relative proportions of 3 and 4 carbon atom compounds, etc. When the percentage of recycle stock is relatively high they may be removed under substantially the same pressure as that obtaining in receiver 26, that is 150 to 300 pounds per square inch. In this case the mixture may be mildly heated during passage through a heater coil 34 positioned in the furnace 35 and brought to a temperature of approximately 100 to 150° F., leaving the heating element through line 36, containing control valve 37, and entering a fractionator or stabilizer 38. By suitably utilizing refluxes in this fractionator the 3 and 4 carbon atom recycle stock may be sharply separated from the gasoline so that the vapor pressure of the final product is at the required point, usually in the neighborhood of ten pounds per square inch by the Reid vapor pressure test. It is, of course, to be understood that any conventional stabilizer may be employed.

The overhead products from the fractionator pass through line 46, control valve 47, condenser 48, line 49 and control valve 50 to receiver 51, which acts as an accumulator for the recycle fractions. Any residue of fixed gases still present at this point may be withdrawn through gas release line 52, containing control valve 53, and utilized as fuel if desired.

Recycle stock accumulating in receiver 51 is returned to the primary heating element. For best results the combined feed blend of this stock with the raw feed should comprise not more than 35% of olefins such as propylene and butylenes. When conditions are properly regulated in the primary cracking plant this percentage will rarely be exceeded since in most cases an equilibrium seems to be established so that the recycle stock contains no more than 25% of 3 and 4 carbon atom olefins, whether the equilibrium is approached from one side or the other. If the percentage of higher olefins in the combined feed exceeds 35% this may be reduced by admixing propane-butane mixtures of a more paraffinic character such as would be obtained, for example, from stabilizer units operating upon straight run gasoline. The importance of this point resides in the fact that if the olefins in the feed are too high there is excessive deposition of carbon in the heating tubes and a corresponding loss in fixed gases of less than 3 carbon atoms under the optimum conditions of treatment. The recycle stock is returned to the heating zone by way of line 54, control valve 55, recycle pump 56, line 57 and valve 58 to enter combined feed line 4.

Gasoline representing the final product of the process appears in the plant under description as a bottom reflux from fractionator 38 from which it may be withdrawn through line 39, containing control valve 40, to receiver 41 with any necessary intermediate cooling although means for effecting this are not shown in the drawing. The receiver is provided with a gas release line 42 containing control valve 43 and a liquid draw line 44, containing control valve 45, for the release of final product.

As exemplifying the relationship obtaining between time, temperature and the per cent of higher olefins in charging stock within a definite temperature interval the following data are introduced. In the experiments furnishing the data, pressure was held constant at 710 pounds per square inch, the recycle stock was 60% of the charge and comprised approximately 25% of propylene and butylenes.

In computing the actual contact time, the following formula was used:

$$\text{Contact time (seconds)} = \frac{t \times P \times Va \times 273}{Vv \times (T+273)}$$

where:

$t$ is the time of the experiment in seconds,
P is the pressure in atmospheres,
$Va$ is the volume of the apparatus (heated zone) in the same units as $Vv$,
$Vv$ is the volume which the charge would have were it completely gasified at 0° C. and 760 mm. pressure plus the volume of the products corrected to 0° C. and 760 mm. divided by two. The two volumes may be expressed in any convenient units so long as $Va$ and $Vv$ are in the same units,
T is the temperature in °C.

The compressibility of the gases was ignored in these calculations. It was assumed at these high temperatures that the perfect gas laws are valid.

The calculated contact time was obtained by using the following empirical formula:

$$\log_{10} t = (7.114 - 0.0105T - 0.0112U) \log_{10} d$$

where:

$t$=Reaction time (contact time) in seconds
T=Temperature in degrees centigrade
U=Per cent higher olefins in the gas. For example $U=10$ for a gas containing 10% higher olefins.
$d$=Wgt. per cent of charge not recovered as recycle stock. For example, if 60 wgt. per cent of the charge was recovered as recycle stock, then $d=40$.

TABLE I

*Relation between per cent of gas reacted, olefin content, temperature and contact time*

| Percent higher olefins | Temperature, °C | Per-cent $d$ | Actual contact time, seconds | Calculated contact time, seconds | Percent deviation of calculated from actual time |
|---|---|---|---|---|---|
| 37 | 500 | 23.5 | 110 | 98 | −10.9 |
| 37 | 500 | 26.5 | 115 | 120 | +4.35 |
| 37 | 525 | 37.5 | 70 | 72 | +2.8 |
| 37 | 525 | 40.4 | 75 | 78 | +4.3 |
| 37 | 525 | 40.6 | 74 | 78 | +5.4 |
| 28 | 525 | 35.5 | 107 | 97 | −9.35 |
| 28 | 550 | 46.7 | 67.7 | 53 | −21.7 |
| 28 | 550 | 45.2 | 66.2 | 51 | −23.0 |
| 24 | 525 | 32.8 | 126 | 105 | −16.7 |
| 24 | 525 | 38.3 | 143 | 129 | −9.8 |
| 24 | 537 | 44.2 | 96 | 100 | +4.2 |
| 24 | 537 | 34.0 | 86 | 72 | −16.3 |
| 24 | 537 | 26.0 | 67 | 52 | −22.2 |
| 24 | 550 | 37.6 | 53.5 | 49 | −8.4 |
| 24 | 550 | 34.7 | 45 | 45 | 0 |
| 24 | 550 | 42.5 | 57.3 | 58 | 0 |
| 0 | 525 | 40 | 287 | 335 | +23.6 |

Average deviation=−4.5%.

The following experimental examples are characteristic of results obtainable by the present process.

*Example I*

Using a charging stock which contains no olefins, having an average molecular weight of 60, gives a combined feed containing 16% higher olefins. This combined feed requires a heating time of 120 seconds at 537° C. (1000° F.). At 550° C. (1022° F.) only 75 seconds are necessary when using a pressure of 710 pounds per square inch in both cases. In this case a yield of 10 gallons per 1000 cubic feet of gas mixture was obtained, or 300 barrels of gasoline from 1000 barrels of liquefied charging stock. The liquid product contained 90% gasoline with an A. P. I. gravity of 61.5 at 60° F. and a blending octane number (motor method) of 93. The Engler distillation of the gasoline fraction follows:

| | |
|---|---|
| I. B. P. °F. | 87 |
| 10% | 110 |
| 20 | 124 |
| 50 | 182 |
| 90 | 320 |
| E. P. °F. | 407 |
| Percent over | 96.5 |
| Percent loss | 2.5 |
| Percent bottoms | 1.0 |

*Example II*

Using a charging stock which contains 37% higher olefins, and has an average molecular weight of 51, gives a combined feed having 28% olefins. At 525° C. (977° F.) a time factor of 120 seconds is necessary while at 537° C. a time of 72 seconds is necessary for 40% conversion at 710 pounds per square inch pressure. The yield in this case is about eight gallons of liquid product per 1000 cubic feet of stock charged. The product contains 90% gasoline which has an A. P. I. gravity of 64.0 and a blending octane number (motor method) of 93. The Engler distillation follows:

| | |
|---|---|
| I. B. P. °F | 89 |
| 10% | 108 |
| 20 | 119 |
| 50 | 167 |
| 90 | 309 |
| E. P. °F | 392 |
| Percent over | 97.0 |
| Percent bottoms | 1.0 |
| Percent loss | 2.0 |

It will be noticed that the yield of liquid in the first example is 10 gallons per 1000 cubic feet of gas reacted while in the second case the yield is 8 gallons per 1000 cubic feet of gas reacted. In the first example the gas has an average molecular weight of 60 while in the second case the average molecular weight was 50. Thus, the yield of liquid products is dependent on the molecular weight of the gas charged. For pure methane or pure ethane, the yield of liquid using the conditions described is zero. With pure propane (molecular weight 44) the yield is about two gallons per 1000 cubic feet of gas reacted. If on the other hand the propane contains appreciable amounts of propylene (molecular weight 42), the liquid yield is higher. Thus, the yield of liquid depends on the molecular weight of the gas charged and the amount of olefins present, since it is fairly easy to form liquids from the olefins already in the gas, while the formation of olefins from the paraffins is accompanied by relatively large losses in the form of "non-condensable" gases, particularly if the paraffins have a molecular weight of about 44.

In each of the above examples each 1000 cubic feet of gas reacted, produced 1000–1300 cubic feet of "non-condensable" gas as one of the products of reaction. This "non-condensable" gas has a molecular weight of from 25–30 and a heating value of 1500 B. t. u. per cubic foot.

The foregoing specification, as well as the examples of improved results obtainable by the use of the process, are given for illustrative purposes only, and neither is to be construed as imposing limitations upon the scope of the invention.

What is claimed:

1. A process for producing more valuable products from light hydrocarbon material consisting essentially of hydrocarbons of 3 and 4 carbon atoms, which comprises subjecting said material, in admixture with recycle stock formed as hereinafter set forth, to pyrolytic conversion such as to convert a portion thereof into gasoline boiling hydrocarbons, controlling the reaction conditions of temperature, pressure and time in the conversion step so that only from 20% to 50% by weight of said material undergoes alteration into hydrocarbons of less than 3 and more than 4 carbon atoms, separating from the effluent of the conversion step gaseous hydrocarbons of less than 3 carbon atoms and isolating the same from the process, further separating from said effluent the 3 and 4 carbon atom hydrocarbons, supplying these separated 3 and 4 carbon atom hydrocarbons to the conversion step as said recycle stock, and recovering the hydrocarbons of more than 4 carbon atoms from which the 3 and 4 carbon atom hydrocarbons have been separated.

2. A process for producing more valuable products from light hydrocarbon material consisting essentially of hydrocarbons of 3 and 4 carbon atoms, which comprises subjecting said material, in admixture with recycle stock formed as hereinafter set forth, to pyrolytic conversion at a temperature of from 450° C. to 575° C. and under a pressure of from 25 to 100 atmospheres for a time period such that only from 20% to 50% by weight of said material undergoes alteration into hydrocarbons of less than 3 and more than 4 carbon atoms, separating from the effluent of the conversion step gaseous hydrocarbons of less than 3 carbon atoms and isolating the same from the process, further separating from said effluent the 3 and 4 carbon atom hydrocarbons, supplying these separated 3 and 4 carbon atom hydrocarbons to the conversion step as said recycle stock, and recovering the hydrocarbons of more than 4 carbon atoms from which the 3 and 4 carbon atom hydrocarbons have been separated.

3. A process for producing more valuable products from the propane-butane fractions separated from hydrocarbon gas mixtures which comprises subjecting the propane-butane fraction, in admixture with recycle stock formed as hereinafter set forth, to pyrolytic conversion such as to produce gasoline boiling hydrocarbons, separating from the effluent of the conversion step an intermediate fraction consisting essentially of the 3 and 4 carbon atom hydrocarbons of the effluent, controlling the reaction conditions of temperature, pressure and time in the conversion step so that said intermediate fraction contains an amount of 3 and 4 carbon atom hydrocarbons corresponding to from 50% to 80% by weight of said propane-butane fraction and so that said intermediate fraction contains not more than 25% olefins, supplying said intermediate fraction to the conversion step as said recycle stock, and isolating the remaining portion of said effluent from the process.

4. A process which comprises subjecting a combined feed, formed as hereinafter set forth and consisting essentially of 3 and 4 carbon atom hydrocarbons, to pyrolytic conversion such as to convert a portion thereof into gasoline boiling hydrocarbons, separating from the effluent of the conversion step an intermediate fraction consisting essentially of the 3 and 4 carbon atom hydrocarbons of the effluent, controlling the reaction conditions of temperature, pressure and time in the conversion step so that said intermediate fraction contains not more than 25% olefinic hydrocarbons of 3 and 4 carbon atoms, combining said intermediate fraction with the propane-butane fraction of a hydrocarbon gas mixture and forming from these fractions a mixture containing less than 35% olefins and between 50% and 80% by weight of the intermediate fraction, supplying the last-named mixture to the conversion step as said combined feed, and isolating the remaining portion of said effluent from the process.

5. A process for producing antiknock motor fuel from a normally gaseous hydrocarbon mixture having an average molecular weight between 50 and 60 and comprised predominantly of paraffins of more than two and less than five carbon atoms per molecule, which comprises subjecting said mixture to pyrolytic conversion such as to convert a portion thereof into gasoline boiling hydrocarbons, controlling the reaction conditions of temperature, pressure and time in the conversion step so as to effect the conversion of no more than 50% of the paraffins initially present in said mixture, and separating from the effluent of the conversion step normally liquid hydrocarbons in the gasoline boiling range.

6. A process for producing antiknock motor fuel from a normally gaseous hydrocarbon mixture having an average molecular weight between 50 and 60 and comprised predominantly of paraffins of more than two and less than five carbon atoms per molecule which comprises subjecting said mixture to pyrolytic conversion at from 450° to 575° C. and under pressure in excess of 500 pounds per square inch for such a time as will effect the conversion of no more than 50% of the paraffins initially present in said mixture, and separating from the effluent of the conversion step normally liquid hydrocarbons in the gasoline boiling range.

7. A process for producing antiknock motor fuel from a normally gaseous hydrocarbon mixture having an average molecular weight between 50 and 60 and comprised predominantly of paraffins of more than two and less than five carbon atoms per molecule, which comprises subjecting said mixture to pyrolytic conversion at from 450° to 575° C. and under pressure in excess of 500 pounds per square inch for such a time as will effect the conversion of between 20% and 50% of the paraffins initially present in said mixture, and separating from the effluent of the conversion step normally liquid hydrocarbons in the gasoline boiling range.

8. A process for producing anti-knock motor fuel from a normally gaseous hydrocarbon material comprised predominantly of paraffins of more than two and less than five carbon atoms to the molecule, which process comprises mixing said material with a recycle stock consisting of 3 and 4 carbon atom hydrocarbons, subjecting the mixture to pyrolytic conversion such as to convert a portion thereof into gasoline boiling hydrocarbons, controlling the reaction conditions of temperature, pressure and time in the conversion step so that only from 20% to 50% by weight of said material undergoes alteration into hydrocarbons of less than 3 and more than 4 carbon atoms, separating the effluent of the conversion step into a fraction of normally liquid hydrocarbons, a fraction containing the hydrocarbons of less than 3 carbon atoms and an intermediate fraction consisting of 3 and 4 carbon atom hydrocarbons, removing the first and second mentioned fractions from the process, and returning at least a portion of the intermediate fraction to the conversion step as said recycle stock.

9. A process for producing anti-knock motor fuel from a normally gaseous hydrocarbon material comprised predominantly of paraffins of more than two and less than five carbon atoms to the molecule, which process comprises mixing said material with a recycle stock consisting of 3 and 4 carbon atom hydrocarbons, subjecting the mixture to pyrolytic conversion at a temperature of from 450° C. to 575° C. and under a pressure of from 25 to 100 atmospheres for a time period such that only from 20% to 50% by weight of said material undergoes alteration into hydrocarbons of less than 3 and more than 4 carbon atoms, separating the effluent of the conversion step into a fraction of normally liquid hydrocarbons, a fraction containing the hydrocarbons of less than 3 carbon atoms and an intermediate fraction consisting of 3 and 4 carbon atom hydrocarbons, removing the first and second mentioned fractions from the process, and returning at least a portion of the intermediate fraction to the conversion step as said recycle stock.

10. A process for producing anti-knock motor fuel which comprises separating from a hydrocarbon gas mixture a paraffinic fraction consisting essentially of hydrocarbons of more than two and less than five carbon atoms to the molecule, subjecting said fraction, in admixture with recycle stock formed as hereinafter set forth, to pyrolytic conversion such as to produce gasoline boiling hydrocarbons, separating from the effluent of the conversion step an intermediate fraction consisting essentially of the 3 and 4 carbon atom hydrocarbons of the effluent, controlling the reaction conditions of temperature, pressure and time in the conversion step so that said intermediate fraction contains an amount of 3 and 4 carbon atom hydrocarbons corresponding to from 50% to 80% by weight of said paraffinic fraction and so that said intermediate fraction contains not more than 25% olefins, supplying said intermediate fraction to the conversion step as said recycle stock, and isolating the remaining portion of said effluent from the process.

11. A process which comprises subjecting a combined feed, formed as hereinafter set forth and consisting essentially of 3 and 4 carbon atom hydrocarbons, to pyrolytic conversion such as to convert a portion thereof into gasoline boiling hydrocarbons, separating from the effluent of the conversion step an intermediate fraction consisting essentially of the 3 and 4 carbon atom hydrocarbons of the effluent, controlling the reaction conditions of temperature, pressure and time in the conversion step so that said intermediate fraction contains not more than 25% olefinic hydrocarbons of 3 and 4 carbon atoms, combining said intermediate fraction with a butane-containing, paraffin-predominating fraction separated from a hydrocarbon gas mixture and consisting of hydrocarbons of more than two and less than five carbon atoms to the molecule, said fractions being combined in such proportions as to form a mixture containing less than 35% olefins and between 50% and 80% by weight of the intermediate fraction, supplying the last-named mixture to the conversion step as said combined feed, and isolating the remaining portion of said effluent from the process.

12. The process as defined in claim 5 further characterized in that there is additionally separated from said effluent a fraction consisting of 3 and 4 carbon atom hydrocarbons which fraction is returned to the conversion step for further treatment together with said hydrocarbon mixture.

13. The process as defined in claim 6 further characterized in that there is additionally separated from said effluent a fraction consisting of 3 and 4 carbon atom hydrocarbons which fraction is returned to the conversion step for further treatment together with said hydrocarbon mixture.

14. The process as defined in claim 7 further characterized in that there is additionally separated from said effluent a fraction consisting of 3 and 4 carbon atom hydrocarbons which fraction is returned to the conversion step for further treatment together with said hydrocarbon mixture.

CARL W. VON HELMOLT,
*Administrator de bonis non with will annexed of the Estate of Hans Tropsch, Deceased.*